(12) United States Patent
Kanemitsu et al.

(10) Patent No.: US 11,647,969 B2
(45) Date of Patent: May 16, 2023

(54) MEDICAL IMAGE PROCESSING APPARATUS AND X-RAY IMAGING APPARATUS

(71) Applicant: CANON MEDICAL SYSTEMS CORPORATION, Otawara (JP)

(72) Inventors: Shingo Kanemitsu, Nasushiobara (JP); Hisanori Kato, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 249 days.

(21) Appl. No.: 17/207,875

(22) Filed: Mar. 22, 2021

(65) Prior Publication Data
US 2021/0298693 A1 Sep. 30, 2021

(30) Foreign Application Priority Data

Mar. 24, 2020 (JP) .............................. JP2020-053022

(51) Int. Cl.
*A61B 6/00* (2006.01)
*A61B 6/02* (2006.01)

(52) U.S. Cl.
CPC ............ *A61B 6/025* (2013.01); *A61B 6/4021* (2013.01); *A61B 6/466* (2013.01)

(58) Field of Classification Search
CPC ...................................................... A61B 6/025
See application file for complete search history.

(56) References Cited

FOREIGN PATENT DOCUMENTS

JP   2009-207683 A    9/2009
JP   2009207683 A  *  9/2009

OTHER PUBLICATIONS

JP2009207683A English Translation. 2009 (Year: 2009).*

* cited by examiner

*Primary Examiner* — Dani Fox
(74) *Attorney, Agent, or Firm* — Oblon, McClelland, Maier & Neustadt, L.L.P.

(57) ABSTRACT

The medical image processing apparatus according to the present embodiment includes processing circuitry. The processing circuitry is configured to acquire volume data generated based on tomosynthesis imaging of a subject. The processing circuitry is configured to set a virtual focal point at a position different from a focal position in the tomosynthesis imaging. The processing circuitry is configured to generate a pseudo projection image based on the virtual focal point and the volume data.

17 Claims, 12 Drawing Sheets

1. TOMOSYNTHESIS IMAGING

2. RECONSTRUCTION

3. SETTING OF VIEWPOINT F1

3. SETTING OF VIEWPOINT F2

1. TOMOSYNTHESIS IMAGING

MEDICAL IMAGE PROCESSING APPARATUS AND X-RAY IMAGING APPARATUS

CROSS-REFERENCE TO RELATED APPLICATION

This application is based upon and claims the benefit of priority from Japanese Patent Application No. 2020-053022, filed on Mar. 24, 2020, the entire contents of which are incorporated herein by reference.

FIELD

An embodiment disclosed in the present specification and drawings relates to a medical image processing apparatus and an X-ray imaging apparatus.

BACKGROUND

Conventionally, in an industrial field such as non-destructive inspection or in a medical field such as a medical examination, an X-ray imaging apparatus that generates X-ray image data from transmission data has been widely used. The X-ray imaging apparatus irradiates an examination target (e.g., the chest) of a subject with radiation (typically, X-ray), and detects transmission data, which is the intensity distribution of the radiation transmitted through the examination target. The X-ray imaging apparatus includes an imaging main apparatus and a medical image processing apparatus. The imaging main apparatus performs X-ray irradiation and acquires transmission data. The medical image processing apparatus generates X-ray image data by controlling the imaging main apparatus, performing image processing of transmission data, and the like.

In order to acquire diagnostically useful X-ray image data from X-ray imaging of the chest and cervical spine, it is particularly important to set the distance between focus detectors (SID: Source to Image receptor Distance) that affects the magnification. However, in the conventional X-ray imaging apparatus, it may be difficult to acquire the X-ray image data corresponding to the desired SID due to restrictions on the arrangement of an X-ray tube, an X-ray detector, and the like. In addition, in order to acquire X-ray image data useful for diagnosis from the X-ray imaging of the chest and cervical spine, the position and angle of X-ray incident on the examination target are also important.

Figure 2A:
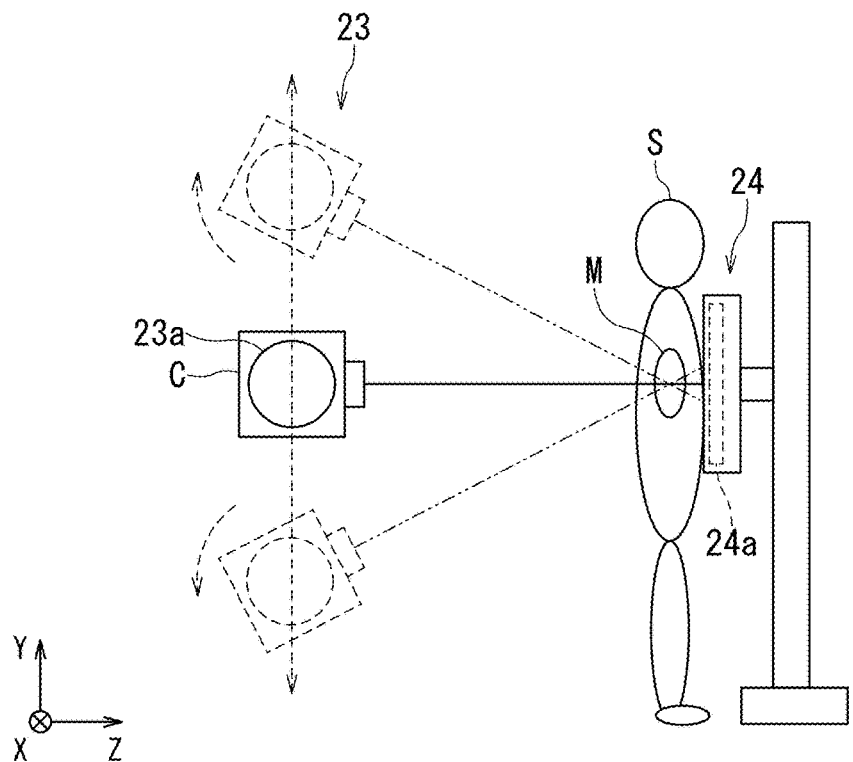
Figure 2B:
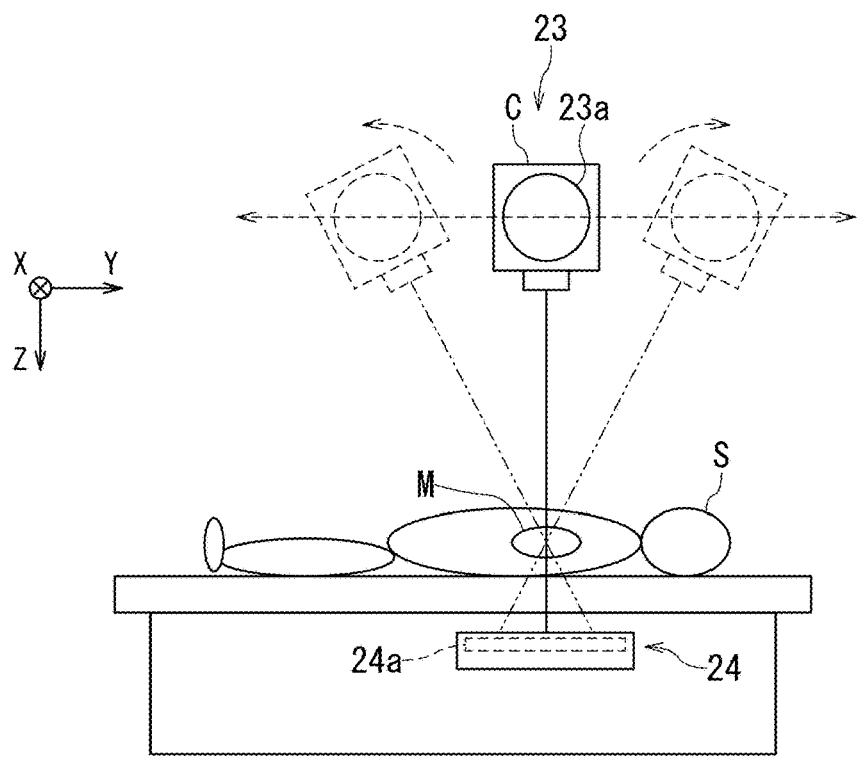

Each of FIGS. 2A and 2B is a diagram showing an arrangement example when tomosynthesis imaging is performed in the medical image processing apparatus according to the first embodiment.

Figure 3:
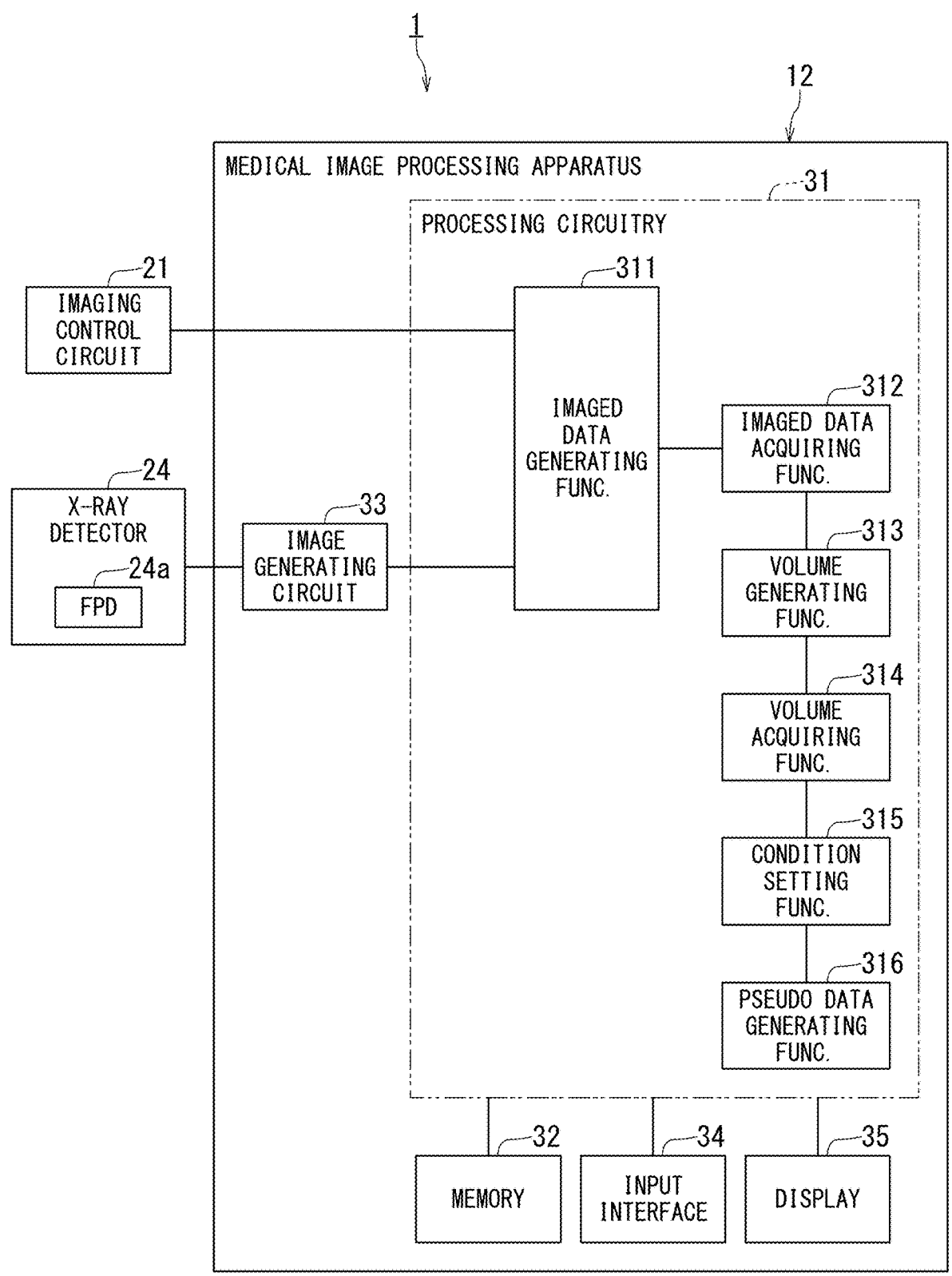

FIG. 3 is a block diagram showing functions of the medical image processing apparatus according to the first embodiment.

Figure 4:
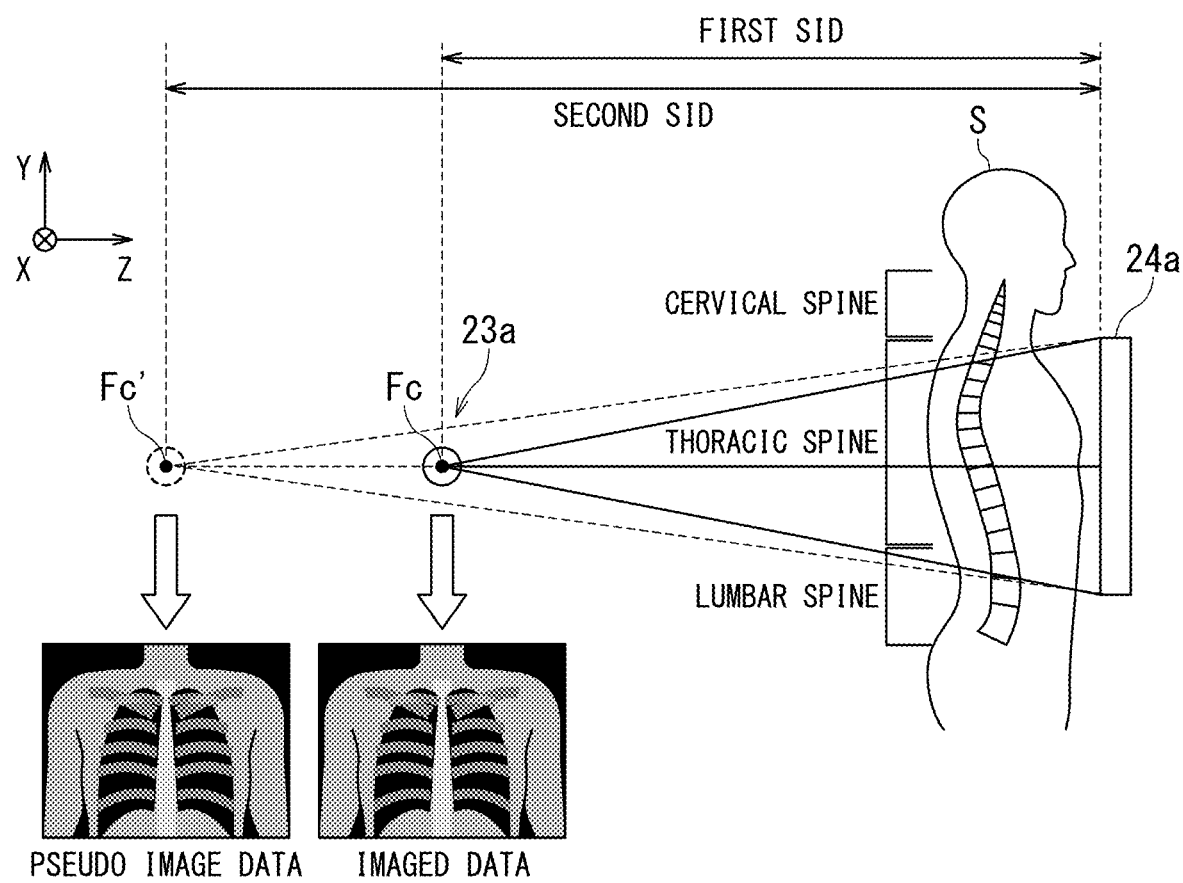

FIG. 4 is a diagram for explaining the concept of a method of generating pseudo image data of the second SID based on imaged data of the first SID in the medical image processing apparatus according to the first embodiment.

Figure 5:
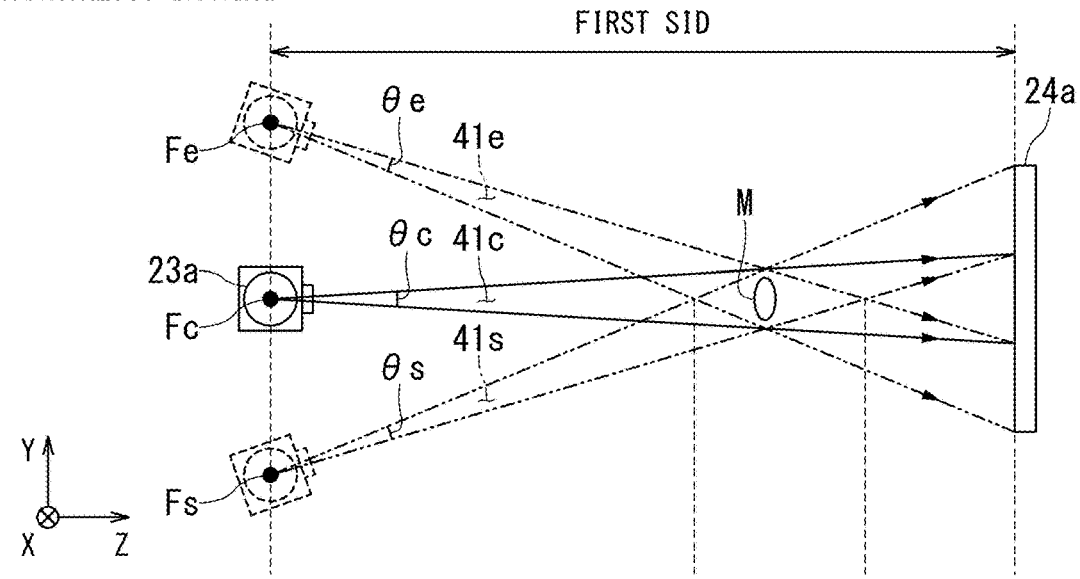
Figure 5:
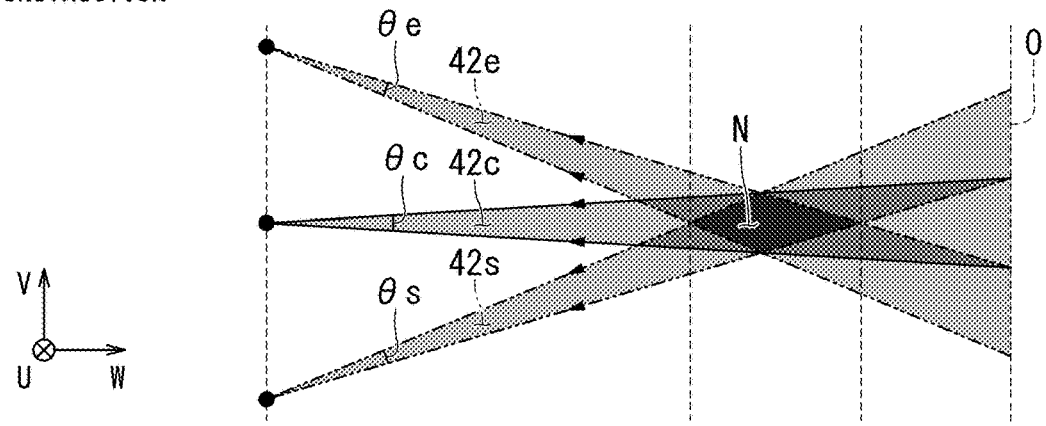
Figure 5:
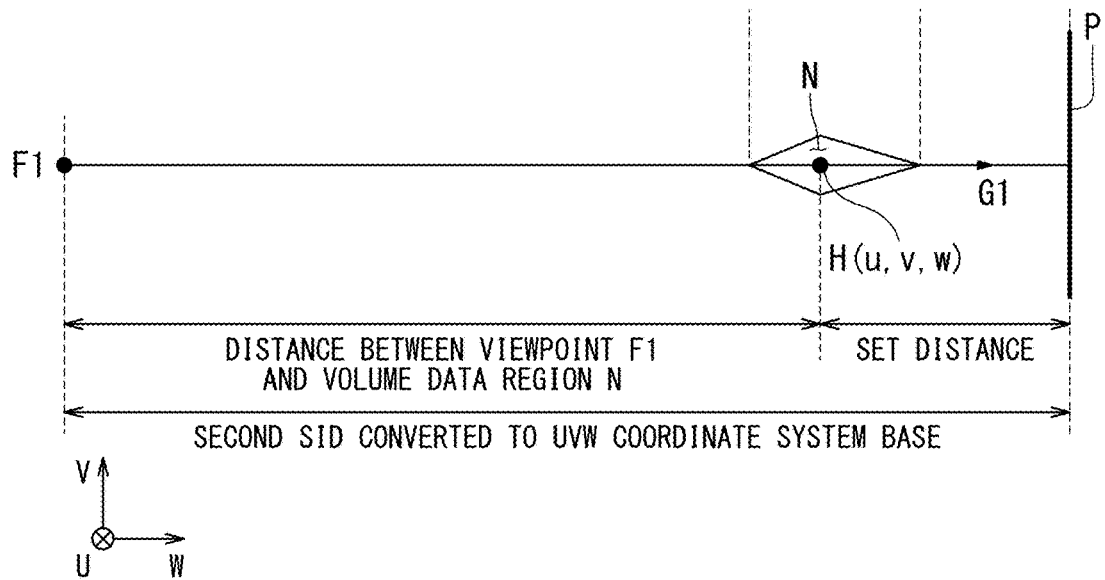

FIG. 5 is a diagram for explaining tomosynthesis imaging, reconstruction, and viewpoint setting in the medical image processing apparatus according to the first embodiment.

Figure 6:
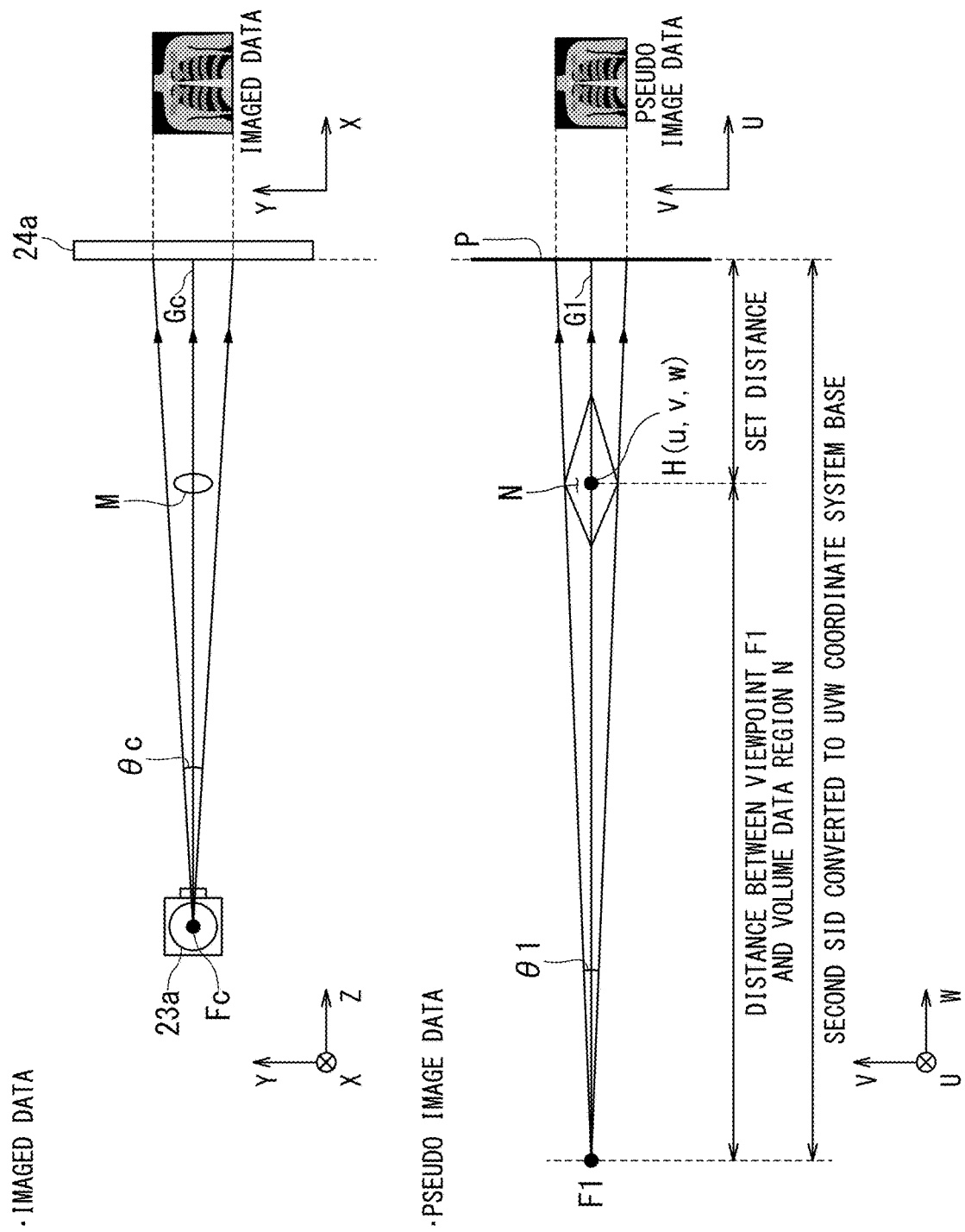

FIG. 6 is a diagram showing a comparative example of imaged data and pseudo image data in the medical image processing apparatus according to the first embodiment.

Figure 7:
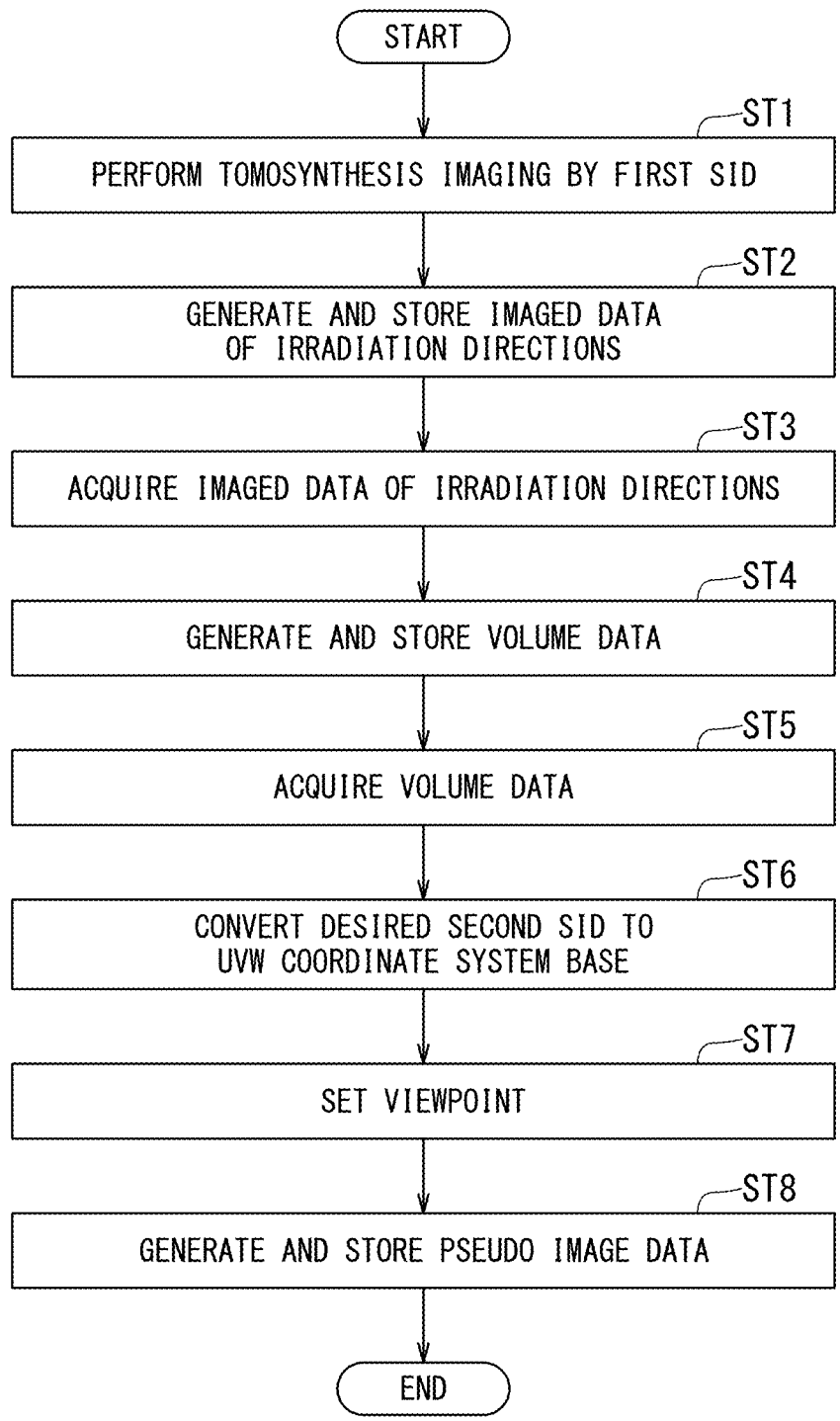

FIG. 7 is a diagram showing an operation of the medical image processing apparatus according to the first embodiment as a flowchart.

Figure 8A:
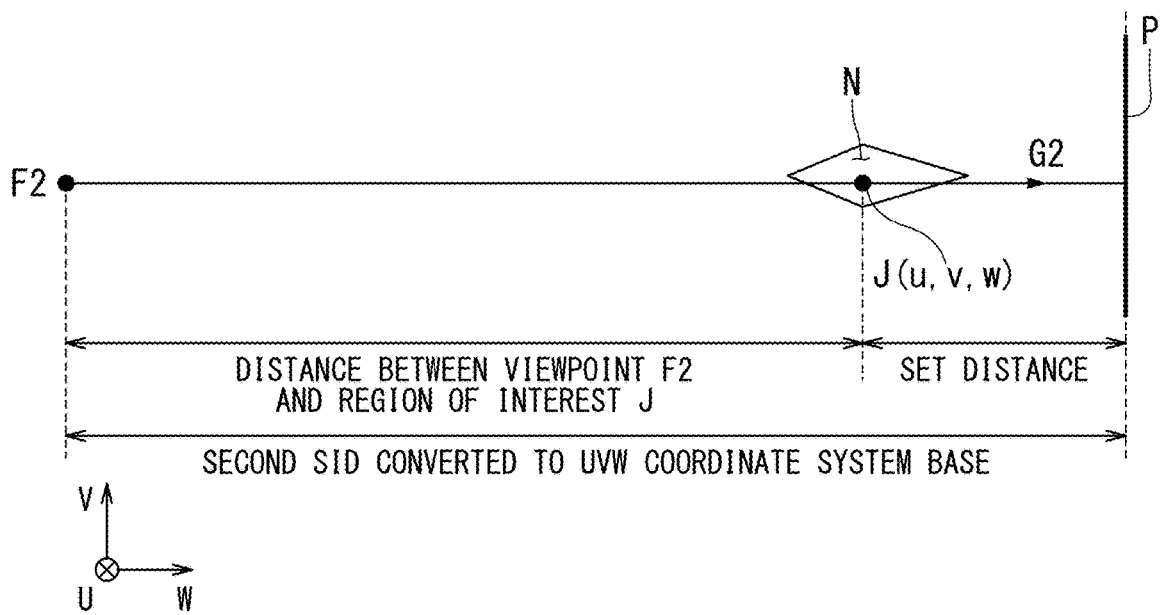
Figure 8B:
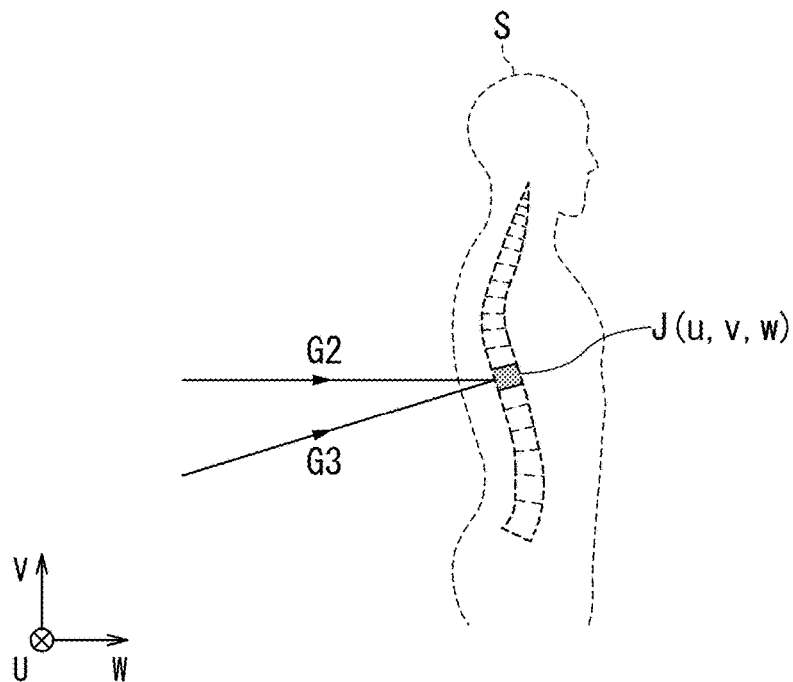

Each of FIGS. 8A and 8B is a diagram for explaining another example of setting the viewpoint in the medical image processing apparatus according to the first embodiment.

Figure 9:
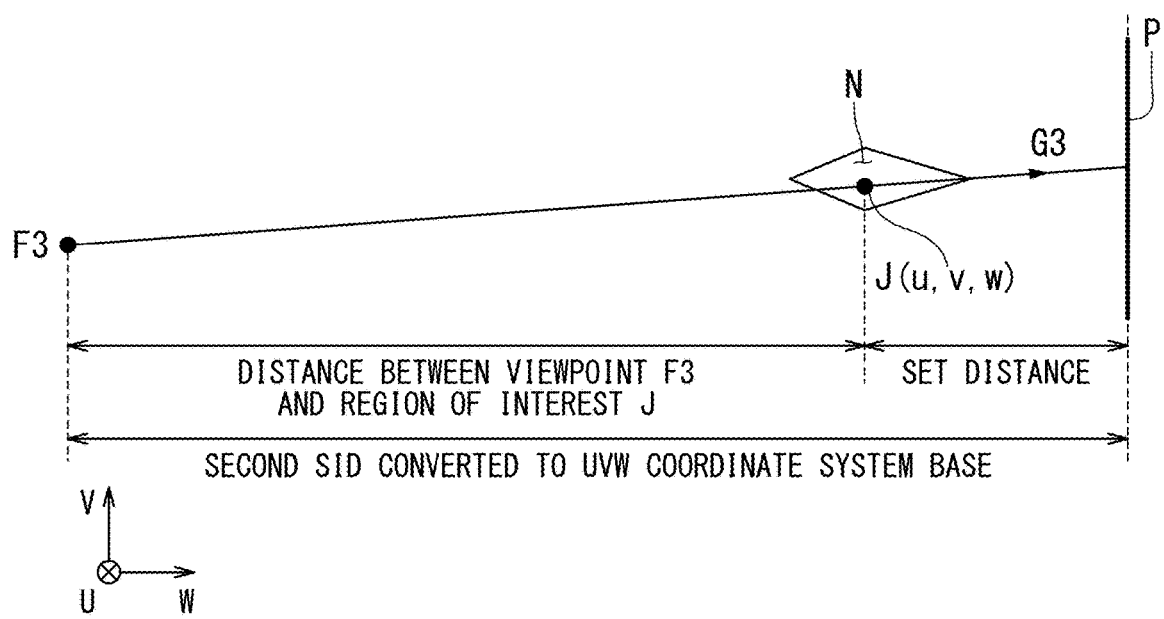

FIG. 9 is a diagram for explaining a method of setting the line-of-sight direction in the medical image processing apparatus according to the first embodiment.

Figure 10:
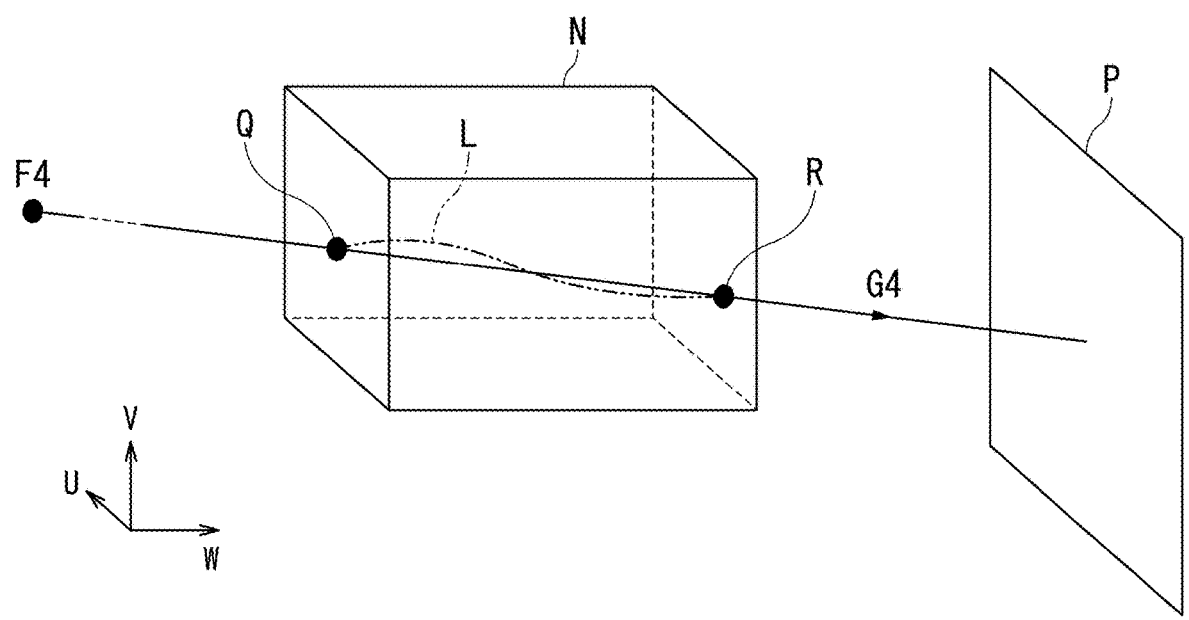

FIG. 10 is a diagram for explaining another method of setting the line-of-sight direction in the medical image processing apparatus according to the first embodiment.

Figure 11:
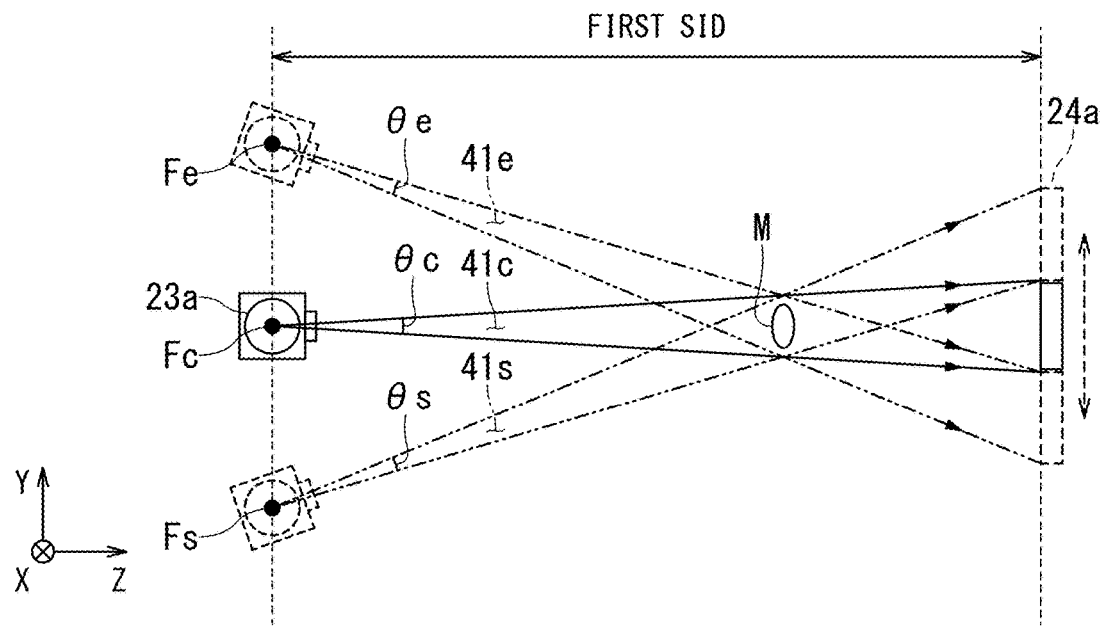

FIG. 11 is a diagram for explaining another method of tomosynthesis imaging in the medical image processing apparatus according to the first embodiment.

Figure 12:
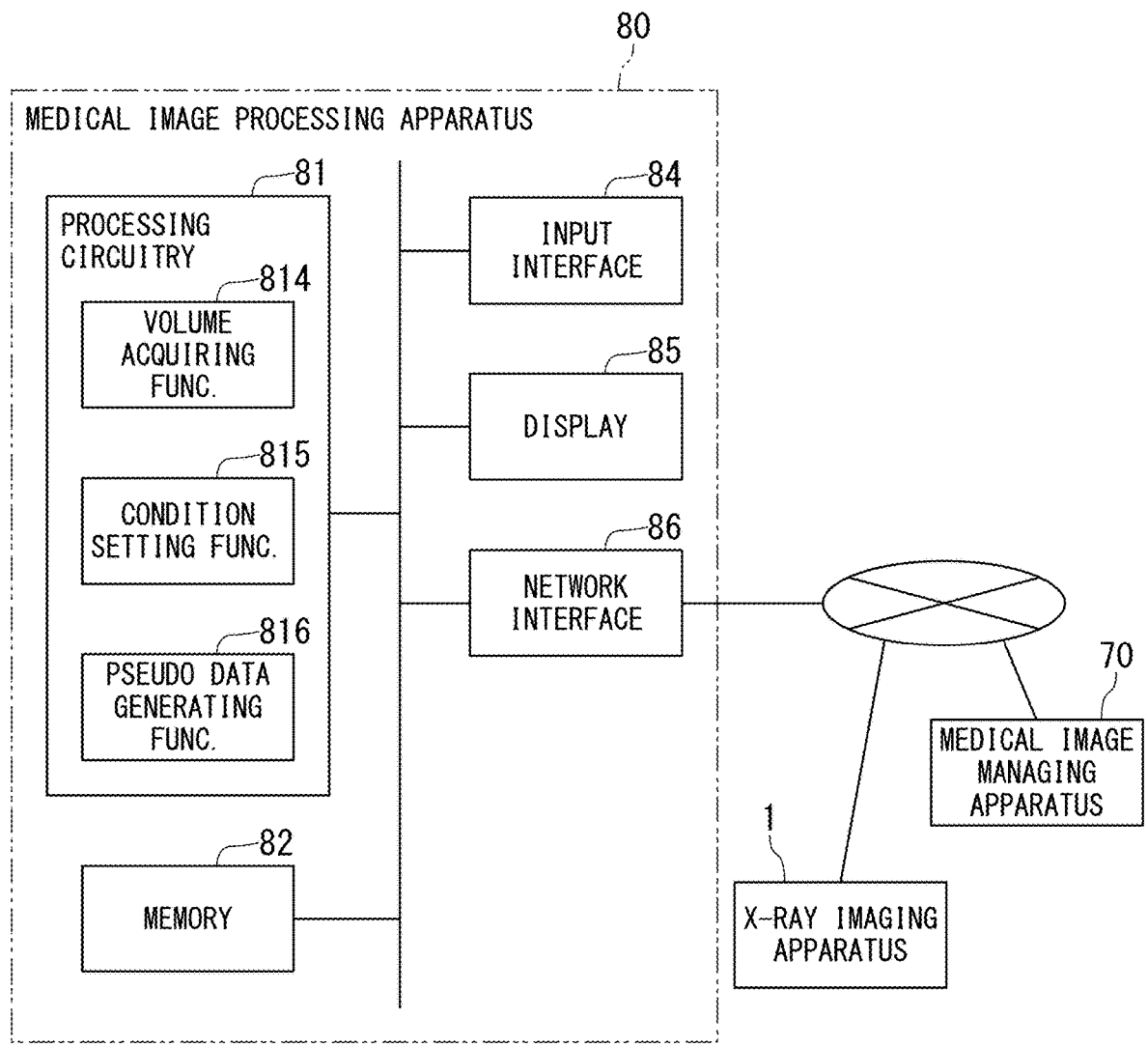

FIG. 12 is a schematic view showing a configuration and function of a medical image processing apparatus according to the second embodiment.

DETAILED DESCRIPTION

A medical image processing apparatus and an X-ray imaging apparatus according to a present embodiment will be described with reference to the accompanying drawings.

The medical image processing apparatus according to the present embodiment includes processing circuitry. The processing circuitry is configured to acquire volume data generated based on tomosynthesis imaging of a subject. The processing circuitry is configured to set a virtual focal point at a position different from a focal position in the tomosynthesis imaging. The processing circuitry is configured to generate a pseudo projection image based on the virtual focal point and the volume data.

First Embodiment

Figure 1:
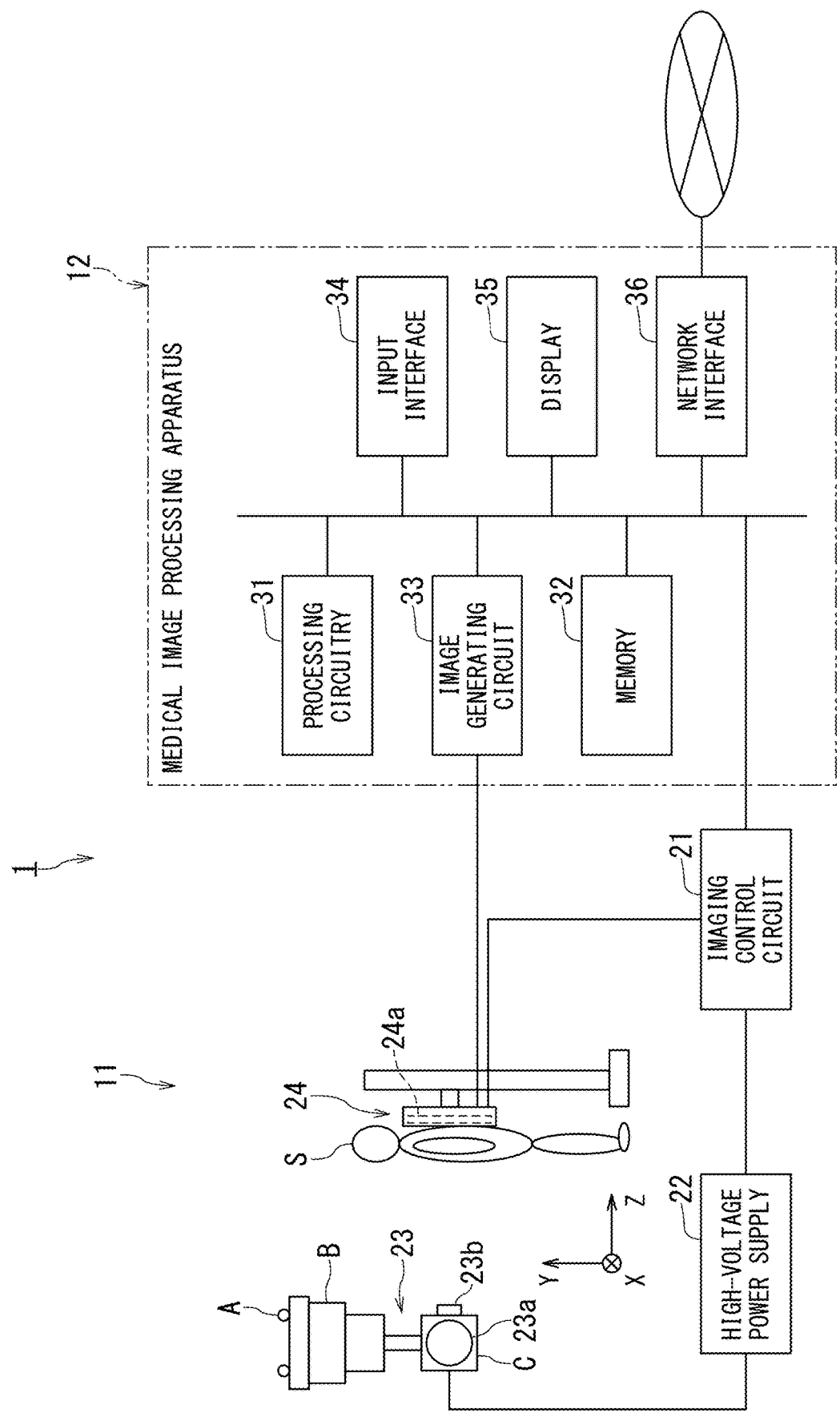
FIG. 1 is a schematic diagram showing a configuration of an X-ray imaging apparatus including a medical image processing apparatus, according to the first embodiment.

FIG. 1 shows an X-ray imaging apparatus 1. The X-ray imaging apparatus 1 includes an imaging main apparatus 11 and a medical image processing apparatus (e.g., a console) 12 according to the first embodiment. The imaging main apparatus 11 includes an imaging control circuit 21, a high-voltage power supply 22, an X-ray irradiator 23, and an X-ray detector 24. The X-ray imaging apparatus 1 performs X-ray imaging of a subject S under the control of the medical image processing apparatus 12.

The left-right direction of the X-ray detector (e.g., FPD 24a) of the X-ray detector 24 is defined as the X-axis direction. The vertical direction of the FPD 24a is defined as the Y-axis direction. The thickness direction of the FPD 24a is defined as the Z-axis direction. Further, FIG. 1 shows a configuration of standing imaging, but the present invention is not limited to this case, and may be in the case of lying imaging. The latter case will be described with reference to FIG. 2B.

The imaging control circuit 21 includes processing circuitry, a memory, and the like. The configuration of the processing circuitry and the memory is the same as that of processing circuitry 31 and a memory 32 of the medical image processing apparatus 12 to be described later, and thus the description thereof will be omitted. The imaging control circuit 21 receives an instruction from the medical image processing apparatus 12, and controls X-ray imaging by controlling the high-voltage power supply 22, the X-ray irradiator 23 and the X-ray detector 24.

The high-voltage power supply 22 supplies high-voltage power to the X-ray source (e.g., an X-ray tube) 23a of the X-ray irradiator 23 under the control of the imaging control circuit 21.

The X-ray irradiator 23 includes an X-ray tube 23a and a movable diaphragm 23b. The X-ray tube 23a receives the supply of high-voltage power from the high-voltage power supply 22, and generates X-rays according to the conditions of the high-voltage power. Under the control of the imaging control circuit 21, the movable diaphragm 23b movably supports the diaphragm blades made of a substance that shields X-rays at the X-ray irradiation port of the X-ray tube 23a. By opening and closing the X-ray irradiation port using the movable diaphragm 23b, the X-ray spread angle (e.g., the spread angles θc, θe and θs shown in FIG. 5) and the like can be changed. The X-ray spread angle θ determines the X-ray irradiation region (e.g., the irradiation regions 41c, 41e and 41s shown in FIG. 5). A radiation quality adjusting filter (not shown) for adjusting the quality of the X-rays generated by the X-ray tube 23a may be provided on the front surface of the X-ray tube 23a.

The X-ray irradiator 23 includes a movable device capable of integrally moving the X-ray tube 23a and the movable diaphragm 23b. The X-ray tube 23a and the movable diaphragm 23b can be moved together manually by an operator holding the X-ray irradiator 23 or automatically by an input operation to the input interface 34.

The X-ray irradiator 23 may include a wheel A as an example of a movable device. The wheel A provided on the upper side of the X-ray tube 23a and the movable diaphragm 23b is movably engaged with the rail that is laid in the X-axis direction and the Z-axis direction on the ceiling of the examination room. In that case, the wheel A can move in the X-axis direction and the Z-axis direction along the ceiling rail. By moving the wheel A in the X-axis direction and the Z-axis direction, the X-ray tube 23a and the movable diaphragm 23b can be integrally moved in the X-axis direction and the Z-axis direction. Due to the sliding movement of the X-ray tube 23a and the movable diaphragm 23b in the Z-axis direction, the position of the X-ray tube 23a in the Z-axis direction, that is, the distance between the focal point of the X-ray tube 23a and FPD 24a (SID: Source Image Distance) can be changed. The SID determines the position of the X-ray focal point (e.g., the focal points Fc, Fe and Fs shown in FIG. 5) in the Z-axis direction.

The X-ray irradiator 23 may include a telescopic structure B as an example of a movable device. The telescopic structure B is extendable in the Y-axis direction. In that case, the lower side of the telescopic structure B can move in the Y-axis direction. By extending and contracting the telescopic structure B in the Y-axis direction, the X-ray tube 23a and the movable diaphragm 23b provided on the lower side of the telescopic structure B can be integrally moved in the Y-axis direction. Due to the sliding movement of the X-ray tube 23a and the movable diaphragm 23b in the Y-axis direction, the position of the focal point of the X-ray tube 23a in the Y-axis direction, that is, the height of the focal point of the X-ray tube 23a (e.g., the focal points Fc, Fe and Fs shown in FIG. 5) can be changed.

The X-ray irradiator 23 may include a rotating structure C as an example of a movable device. The rotating structure C holds the X-ray tube 23a and the movable diaphragm 23b, and is rotatable about an axis that is parallel to the X axis and passes through the focal point. In that case, the rotating structure C can rotate about the X-axis. By rotating the rotating structure C about the X-axis, the X-ray tube 23a held by the rotating structure C and the movable diaphragm 23b can be rotated as one. By the rotational movement of the rotating structure C, the irradiation direction of X-rays with respect to the FPD 24a (e.g., the irradiation direction Gc shown in FIG. 6) can be changed. The irradiation direction is also called a "view".

The X-ray detector 24 includes a flat panel detector (FPD) 24a (shown in FIG. 2) as an X-ray detector and an analog to digital (A/D) conversion circuit (not shown).

The FPD 24a is provided to face the X-ray tube 23a of the X-ray irradiator 23 with its detection surface being parallel to the X-axis and the Y-axis. The FPD 24a includes multiple detection elements for detecting X-rays. The detection elements are arranged in a matrix.

The A/D conversion circuit converts the projection data of the time-series analog signal (video signal) output from the FPD 24a into a digital signal, and outputs it to the medical image processing apparatus 12.

The X-ray detector 24 may include a moving structure (not shown) movable in the z-axis direction as an example of a movable device. By moving the moving structure in the Z-axis direction, the FPD 24a held by the moving structure can be moved in the Z-axis direction. By moving the FPD 24a in the Z-axis direction, the SID, which is the distance between the FPD 24a and the X-ray tube 23a, and the like can be changed.

It should be noted that the X-ray detector 24 may be I. I. (Image Intensifier)-TV system. The I. I.-TV system converts transmitted X-rays and directly incident X-rays into visible light, forms sensitive projection data by doubling the brightness in the process of light-electron-light conversion, and converts optical projection data into electric signals by using a charge coupled device (CCD) image sensor.

As described above, by combining the sliding movement of the rotating structure C in the Y-axis direction and the rotational movement of the rotating structure C, the X-ray imaging apparatus 1 can perform tomosynthesis imaging capable of imaging the chest M from multiple irradiation directions. FIG. 2A shows an arrangement example in the case of performing tomosynthesis imaging while maintaining a predetermined SID in standing imaging. As shown in FIG. 2A, the rotating structure C holding the X-ray tube 23a is slidingly moved in the Y-axis direction (vertical direction), and the rotating structure C is rotationally moved. When the rotating structure C is moved in the upward direction, the rotating structure C is being rotationally moved clockwise. When the rotating structure C is moved in the downward direction, the rotating structure C is being rotationally moved counterclockwise.

FIG. 2B shows an arrangement example in which tomosynthesis imaging is performed while maintaining a predetermined SID in lying imaging. As shown in FIG. 2B, the rotating structure C holding the X-ray tube 23a is slidingly moved in the Y-axis direction (head and foot direction), and the rotating structure C is rotationally moved. When the rotating structure C is moved in the head direction, the rotating structure C is being rotationally moved clockwise. When the rotating structure C is moved in the foot direction, the rotating structure C is being rotationally moved counterclockwise.

As shown in FIGS. 2A and 2B, the FPD 24a can respectively detect each X-rays incident from each irradiation direction (three irradiation directions in FIGS. 2A and 2B). As described above, the X-ray imaging apparatus 1 can perform tomosynthesis imaging to acquire multiple imaged data corresponding to multiple irradiation directions. Further, as will be described later, it is possible to generate volume data from multiple acquired imaged data.

Returning to the description of FIG. 1, the medical image processing apparatus 12 includes processing circuitry 31, a memory 32, an image generating circuit 33, an input interface 34, a display 35, and a network interface 36. The image generating circuit 33 is composed of an application specific integrated circuit (ASIC) or the like. However, the present invention is not limited to this case, and all or part of the functions of the image generating circuit 33 may be realized by the processing circuitry 31 executing the program.

The processing circuitry 31 controls whole operations of the X-ray imaging apparatus 1. The processing circuitry 31 may refer to a processor such as a dedicated or general-purpose central processing unit (CPU), a microprocessor unit (MPU), a graphics processing unit (GPU), or the like. The processing circuitry 31 may refer to an ASIC, a programmable logic device, or the like. The programmable logic device is, for example, a simple programmable logic device (SPLD), a complex programmable logic device (CPLD), and a field programmable gate array (FPGA).

Further, the processing circuitry 31 may be constituted by a single circuit or a combination of independent circuit elements. In the latter case, the memory 32 may be provided individually for each circuit element, or a single memory 32 may store programs corresponding to the functions of the circuit elements.

The memory 32 is constituted by a semiconductor memory element such as a random-access memory (RAM), a flash memory, a hard disk, an optical disk, or the like. The memory 32 may be constituted by a portable medium such as a universal serial bus (USB) memory and a digital video disk (DVD). The memory 32 stores various processing programs (including an operating system (OS) and the like besides the application program) used in the processing circuitry 31 and data necessary for executing the programs. In addition, the OS may include a graphical user interface (GUI) which allows the operator to frequently use graphics to display information on the display 35 to the operator and can perform basic operations using the input interface 34. The memory 32 is an example of a storage.

Under the control of the processing circuitry 31, the image generating circuit 33 performs logarithmic conversion processing (LOG processing) on the transmission data output from the A/D conversion circuit (not shown) of the X-ray detector 24 of the imaging main apparatus 11, performs addition processing as needed, and generates X-ray image data as imaged data. Further, the image generating circuit 33 performs image processing on the generated imaged data under the control of the processing circuitry 31. Examples of the image processing include enlargement/gradation/spatial filter processing of data, minimum/maximum value tracing processing of data accumulated in time series, and addition processing for removing noise.

The image generating circuit 33 stores the generated imaged data in a storage such as a memory 32. The image generating circuit 33 is an example of an image generator.

The input interface 34 includes an input device operable by an operator, and a circuit for inputting a signal from the input device. The input device may be a trackball, a switch, a mouse, a keyboard, a touch pad for performing an input operation by touching an operation surface, a touch screen in which a display screen and a touch pad are integrated, a non-contact input circuit using an optical sensor, an audio input circuit, and the like. When the input device is operated by the operator, the input interface 30 generates an input signal corresponding to the operation and outputs it to the processing circuitry 31. The input interface 34 is an example of an input unit.

The display 35 displays various information. For example, the display 35 outputs imaged data generated by the image generating circuit 33, pseudo image data to be described later, a graphical user interface (GUI) for receiving various operations from the operator, and the like. The display 35 may be a liquid crystal display, a cathode ray tube (CRT) display, an organic light emitting diode (OLED) display, or the like. The display 35 is an example of a display unit.

The network interface 36 implements various information communication protocols according to the network form. The network interface 36 connects the X-ray imaging apparatus 1 and other apparatuses such as the external image server (not shown) according to these various protocols. An electrical connection or the like via an electronic network is applied to this connection. In the present embodiment, the electronic network refers to an entire information communication network using telecommunications technology. The electronic network includes a wired/wireless hospital backbone local area network (LAN) and the Internet network, as well as a telephone communication line network, an optical fiber communication network, a cable communication network, a satellite communication network, or the like. The network interface 36 is an example of a network connecting unit.

Subsequently, functions of the medical image processing apparatus 12 will be described.

As shown in FIG. 3, the processing circuitry 31 reads and executes a computer program stored in the memory 32 or directly embedded in the processing circuitry 31, thereby realizing an imaged data generating function 311, an imaged data acquiring function 312, a volume generating function 313, a volume acquiring function 314, a condition setting function 315, and a pseudo data generating function 316. Hereinafter, the case where the functions 311 to 316 function as software will be described as an example, but all or a part of the functions 311 to 316 may be realized by a circuit such as an ASIC. Further, all or a part of the functions 311 to 316 may be realized by the imaging control circuit 21 of the imaging main apparatus 11.

First, the significance of the X-ray imaging apparatus 1 will be described. According to one imaged data by X-ray imaging from one position of the X-ray tube 23a, it is possible to acquire the imaged data regarding the examination target M of the subject S by one X-ray imaging. Here, in X-ray imaging when the examination target M is the chest, the SID is important with respect to the incident position, it is important to the center of the 7th to 8th thoracic spine with the x-rays, using an appropriate SID.

However, it may be difficult to increase the SID due to the degree of freedom in the layout of the imaging main apparatus 11. For example, compared with the imaging main apparatus 11 for standing imaging, it may be more difficult to increase the SID of the imaging main apparatus 11 for lying imaging due to structural restrictions. Therefore, based on the first projection image data (referred to as "imaged data") of the first SID, the X-ray imaging apparatus 1 generates the second projection image data (referred to as "pseudo projection image data" or "pseudo image data") of the second SID, which is larger than the first SID.

FIG. 4 is a diagram for explaining the concept of a method of generating the pseudo image data of the second SID based on the imaged data of the first SID.

FIG. 4 shows the relationship between the arrangement by the first SID and the arrangement by the second SID. FIG. 4 shows an FPD 24a and an X-ray tube 23a of focal Fc that is placed relative to the FPD 24a according to the first SID. The imaged data is acquired based on the X-ray imaging by the first SID. Here, in the chest imaging of the subject, since the cervical spine, the thoracic spine, and the lumbar spine are curved, the incident positions and the angles to these parts are not constant.

In general, when imaging the cervical spine, the thoracic spine, and the lumbar spine, it may be desirable to perform an X-ray imaging from the X-ray tube 23a of the focal point Fc' which is arranged with respect to the FPD 24a according to the second SID that is larger than the first SID. For example, when the examination target M is the chest, the incident direction of X-rays by which the boundary between the upper lobe and the middle lobe of the lung is shown in a thin line is considered appropriate in order to acquire an image suitable for diagnosis. For that purpose, it is preferable to set the X-ray focus on a position about 2000 [mm] horizontally away from the center of the 7th to 8th thoracic spine. Such a setting also is an important imaging factor in terms of comparison with a past image. However, due to the degree of freedom in the layout of the imaging main apparatus 11, it may be difficult to set the SID to about 2000 [mm], which is larger than the first SID.

Therefore, the X-ray imaging apparatus 1 generates volume data based on the imaged data of the first SID, and generates pseudo image data of the second SID larger than the first SID.

Returning to the description of FIG. 3, the imaged data generating function 311 has a function of controlling the imaging control circuit 21 of the imaging main apparatus 11 to execute tomosynthesis imaging with the first SID, and a function of controlling the image generating circuit 33 to generate multiple X-ray projection data corresponding to multiple irradiation directions as multiple imaged data respectively, based on the transmission data acquired by the tomosynthesis imaging. In addition, the imaged data generating function 311 may have a function of storing multiple imaged data in the memory 32. The imaged data generating function 311 is an example of an imaged data generating unit.

The tomosynthesis imaging will be described with reference to the upper part of FIG. 5. The upper part of FIG. 5 shows three focal points Fc, Fe and Fs of the X-ray tube 23a arranged with respect to the FPD 24a according to the first SID in the real coordinate system, that is, the XYZ coordinate system. The X-rays generated at the focal point Fc enter the examination target M in the irradiation region 41c based on the spread angle θc, and reach the vicinity of the center of the FPD 24a in the Y-axis direction. The X-rays generated at the focal point Fe enter the examination target M in the irradiation region 41e based on the spread angle θe and reach the negative side of the Y-axis of the FPD 24a. The X-rays generated at the focal point Fs enter the examination target M in the irradiation region 41s based on the spread angle θs, and reach the positive side of the Y-axis of the FPD 24a.

Returning to the description of FIG. 3, the imaged data acquiring function 312 has a function of acquiring multiple imaged data generated by the imaged data generating function 311 from the memory 32. The imaged data acquiring function 312 is an example of an imaged data acquiring unit.

The volume generating function 313 has a function of generating volume data based on the multiple imaged data acquired by the imaged data acquiring function 312. For example, the volume generating function 313 aligns and arranges the multiple imaged data, that is, projection profiles, in the UVW coordinate system corresponding to the XYZ coordinate system, and performs back-projection processing on the projection profiles. Accordingly, the volume generating function 313 generates volume data in the three-dimensional space of the UVW coordinate system. Before the back projection processing, each of projection profiles may be filtered to cancel the edges.

Further, the volume generating function 313 may include a function of storing the volume data in the memory 32. The volume generating function 313 is an example of a volume generating unit.

Reconstruction (e.g., back projection processing) will be described with reference to the middle part of FIG. 5. The middle part of FIG. 5 shows a volume data region N generated at a position separated from the detection surface O of the FPD 24a in the negative direction of the W axis by a certain distance in the data space coordinate system, that is, the UVW coordinate system. The data region 42c is at a position corresponding to the irradiation region 41c (shown in the upper part) extending from the focal Fc to the detection surface O. The data region 42e is at a position corresponding to the irradiation region 41e (shown in the upper part) extending from the focal point Fe to the detection surface O. The data region 42s is at a position corresponding to the irradiation region 41s extending from the focal point Fs to the detection surface O. The volume data region N is generated so as to include the overlapping positions of the data regions 42c, 42e, and 42s.

Hereinafter, a case where the size of the XYZ coordinate system and the size of the UVW coordinate system have a one-to-one correspondence will be described.

The volume data region N herewith refers to a data region that the data regions 42c, 42e and 42s all overlap, but is not limited to that case. The volume data region N may be a region that includes a region where the data regions 42c, 42e and 42s all overlap.

Returning to the description of FIG. 3, the volume acquiring function 314 has a function of acquiring the volume data generated by the volume generating function 313 from the memory 32. That is, the volume acquiring function 314 has a function of acquiring volume data generated based on tomosynthesis imaging of the subject. The volume acquiring function 314 is an example of a volume acquiring unit.

The condition setting function 315 has a function of setting a virtual focal point at a position different from the focal position in tomosynthesis imaging. For example, the condition setting function 315 has a function of setting a viewpoint as the virtual focal point based on a second SID that is larger than the first SID. Specifically, the condition setting function 315 converts the second SID of the XYZ coordinate system into the UVW coordinate system base, and sets the viewpoint based on the converted second SID of the UVW coordinate system. The condition setting function 315 is an example of a condition setting unit.

The pseudo data generating function 316 has a function of generating pseudo image data based on the virtual focal point set by the condition setting function 315 and the volume data acquired by the volume acquiring function 314. For example, the pseudo data generating function 316 has a function of projecting the volume data acquired by the volume acquiring function 314 from the viewpoint set by the condition setting function 315 along the line-of-sight direction (projection direction), and generating projection data as pseudo image data. Specifically, the pseudo data generating function 316 generates pseudo image data by projecting the volume data of the UVW coordinate system from the viewpoint of the UVW coordinate system. The pseudo data generating function 316 is an example of a pseudo data generating unit.

The setting of the viewpoint will be described with reference to the lower part of FIG. 5. The lower part of FIG. 5 shows the projection plane P of the UVW coordinate system corresponding to the detection surface O (shown in the middle part) of the FPD 24a. Further, the lower part of FIG. 5 shows the second SID of the UVW coordinate system converted from the second SID of the XYZ coordinate system (e.g., 2000 [mm]). The second SID can also be set as infinity. In that case, instead of central projection having the viewpoint as the base point, parallel projection that is substantially parallel to the line-of-sight direction becomes possible.

As shown in the lower part of FIG. 5, the condition setting function 315 calculates the distance acquired by subtracting the set distance from the second SID converted into the UVW coordinate system, and sets a position separated from the volume data region N (e.g., the reconstruction center H) by a calculated distance as the viewpoint F1. The set distance may be a predetermined constant distance, or may be a distance between the projection plane P calculated based on the second SID and the reconstruction center H. It should be noted that the present invention is not limited to these cases. The condition setting function 315 may regard the set distance as "0". In that case, the condition setting function 315 sets a position separated from the position of the projection plane P by a distance corresponding to the second SID converted into the UVW coordinate system as the viewpoint F1. Here, the line-of-sight direction G1 may be corresponding to a direction orthogonal to the detection surface of the FPD 24a in the XYZ coordinate system, that is, a positive direction of the W-axis.

Returning to the description of FIG. 3, the pseudo data generating function 316 has a function of displaying the pseudo image data as a pseudo image on the display 35. Further, the pseudo data generating function 316 may has a function of storing the pseudo image data in the memory 32. The pseudo data generating function 316 is an example of a pseudo data generating unit.

The upper part of FIG. 6 shows a method of generating imaged data generated by actual X-ray imaging. From the focal point Fc of the X-ray tube 23a arranged by the first SID, X-rays are irradiated in the irradiation direction Gc, which is the positive direction of the Z-axis, at a spread angle θc, and the X-rays are detected by the FPD 24a. Accordingly, imaged data based on the first SID is generated.

The lower part of FIG. 6 shows a method of generating pseudo image data generated from the volume data region N. The volume data region N is projected onto the projection plane P at a spread angle θ1 along the line-of-sight direction G1 which is the positive direction of the W axis from the viewpoint F1 set by the second SID converted to the UVW coordinate system. The spread angle θ1 may be set so that the projection size on the projection plane P is about the same as the irradiation size of X-rays on the detection surface in the XYZ coordinate system. Accordingly, pseudo image data based on the second SID is generated.

As described above, according to the X-ray imaging apparatus 1, even if it is difficult to increase the SID due to the degree of freedom in the layout of the imaging main apparatus 11, it is possible to generate and display the pseudo image data of a second SID larger than the first SID based on the imaged data of the first SID. As a result, even if the examination target M is the chest or the like, it is possible to provide the operator with an image that is easy to diagnose.

Subsequently, an operation of the medical image processing apparatus 12 will be described.

FIG. 7 is a diagram showing the operation of the medical image processing apparatus 12 in a flowchart. In FIG. 7, reference numerals with numbers added to "ST" indicate each step in the flowchart.

The imaged data generating function 311 controls the imaging control circuit 21 of the imaging main apparatus 11 to perform tomosynthesis imaging by the first SID using the imaging main apparatus 11 (step ST1). The tomosynthesis imaging by the first SID has already been described using the upper part of FIG. 5. The imaged data generating function 311 controls the image generating circuit 33 to generate multiple imaged data corresponding to multiple irradiation directions based on the transmission data acquired by the tomosynthesis imaging in step ST1, and stores multiple imaged data in the memory 32 (step ST2).

The imaged data acquiring function 312 acquires the multiple imaged data generated and stored in step ST2 from the memory 32 (step ST3). The volume generating function 313 generates volume data based on the multiple imaged data acquired in step ST3, and stores the volume data in the memory 32 (step ST4). The reconstruction of the volume data has already been described using the middle part of FIG. 5.

The volume acquiring function 314 acquires the volume data generated and stored in step ST4 from the memory 32 (step ST5). The condition setting function 315 converts the second SID of the XYZ system to the UVW coordinate system base (step ST6). The condition setting function 315 sets a viewpoint in the projection process described later based on the second SID of the UVW coordinate system converted in step ST6 (step ST7). The setting of the viewpoint has already been explained using the lower part of FIG. 5.

The pseudo data generating function 316 generates pseudo image data by projecting the volume data of the UVW coordinate system acquired in step ST5 from the viewpoint set in step ST7, and displays the pseudo image data as a pseudo image on the display 35 (step ST8).

The medical image processing apparatus 12 such as a console can generate pseudo image data corresponding to the second SID larger than the first SID based on the imaged data acquired by the first SID. As a result, according to the medical image processing apparatus 12, it is possible to provide the operator with pseudo image data useful for diagnosis in consideration of the incident position and the incident angle on the examination target M.

(First Modification)

As shown in the lower part of FIG. 5, the X-ray imaging apparatus 1 sets the viewpoint F1 based on a predetermined position (e.g., the reconstruction center) H of the volume data region N, but it is not limited to that case. For example, the condition setting function 315 of the X-ray imaging apparatus 1 may detect a region of interest J, which may be the center of the 7th to 8th thoracic spine, using the volume data region N. In that case, the condition setting function 315 sets the viewpoint based on the region of interest J.

The condition setting function 315 may use machine learning for detecting the region of interest J. Further, as machine learning, deep learning using a multi-layer neural network such as a convolutional neural network (CNN) or a convolutional deep belief network (CDBN) may be used.

For example, the condition setting function 315 creates a model by passing a large amount of volume data including the thoracic spine through machine learning, inputs the volume data acquired in step ST5 (shown in FIG. 7) into the model, and outputs the coordinates (u, v, w) of the region of interest J such as the center of the 7th to 8th thoracic spine based on the result of comparison performed by the machine learning.

FIG. 8A shows a region of interest J such as the center of the 7th to 8th thoracic spine set in the volume data region N. The viewpoint F2 and the line-of-sight direction G2 are set so as to simulate horizontal X-ray-irradiation on the center of the 7th to 8th thoracic spine. The condition setting function 315 calculates the distance acquired by subtracting the set distance from the second SID converted into the UVW coordinate system, and sets a position separated from the region of interest J of the volume data region N by a calculated distance as the viewpoint F2. However, it is not limited to this case. The condition setting function 315 may regard the set distance as "0". In that case, the condition setting function 315 sets the position separated from the position of the projection plane P by the distance corresponding to the second SID converted into the UVW coordinate system as the viewpoint F2. Here, the line-of-sight direction G2 may be corresponding to a direction orthogonal to the detection surface of the FPD 24a in the XYZ coordinate system, that is, a positive direction of the W-axis (shown in FIG. 8B).

The condition setting function 315 may set the region of interest in the volume data (or the pseudo image data), and modify the viewpoint to a position where the contrast of the region of interest meets a predetermined reference.

Further, the condition setting function 315 may set viewpoints to be projected in line-of-sight directions orthogonal to regions of interest in the volume data, respectively. In that case, the pseudo data generating function 316 generates multiple pseudo image data based on the set viewpoints and line-of-sight directions, and synthesizes the multiple pseudo image data to generate image data.

According to the first modification of the medical image processing apparatus 12 such as a console, pseudo image data centered on the region of interest J such as the center of the 7th to 8th thoracic spine can be generated. As the result, it is possible to provide the operator with pseudo image data useful for diagnosis.

(Second Modification)

As shown in the lower part of FIG. 5, the X-ray imaging apparatus 1 sets the line-of-sight direction G1 to be corresponding to the direction orthogonal to the detection surface of the FPD 24a in the XYZ coordinate system, that is, the positive direction of the W-axis. However, it is not limited to this case. The condition setting function 315 may set the line-of-sight direction in addition to the viewpoint. In that case, the pseudo data generating function 316 generates pseudo image data by projecting the volume data along the set line-of-sight direction.

For example, the condition setting function 315 of the X-ray imaging apparatus 1 may detect the region of interest J such as the center of the 7th to 8th thoracic spine using the volume data region N, set the line-of-sight direction in consideration of the incident position and the incident angle to the region of interest J, and set the viewpoint based on to the line-of-sight direction. Since the method for detecting the region of interest J is the same method as described in the first modification, the description thereof will be omitted.

FIG. 9 shows a region of interest J such as the center of the 7th to 8th thoracic spine set in the volume data region N. The line-of-sight direction G3 is set in the direction orthogonal to the region of interest J so as to simulate vertical X-ray-irradiation on the center of the 7th to 8th thoracic spine. The condition setting function 315 calculates the distance acquired by subtracting the set distance from the second SID converted into the UVW coordinate system, and sets a position separated from the region of interest J in the volume data region N by a calculated distance as the viewpoint F3. However, it is not limited to this case. The condition setting function 315 may regard the set distance as "0". In that case, the condition setting function 315 sets a position separated from the projection plane P by a distance corresponding to the second SID converted into the UVW coordinate system as the viewpoint F3. Here, the line-of-sight direction G3 has an angle from the direction corresponding to the direction orthogonal to the detection surface of the FPD24a in the XYZ coordinate system, that is, the positive direction of the W-axis (shown in FIG. 8B).

According to the second modification of the medical image processing apparatus 12 such as a console, pseudo image data can be generated when X-rays are incident substantially perpendicularly onto the region of interest j such as the center of the 7th to 8th thoracic spine. As a result, it is possible to provide the operator with pseudo image data useful for diagnosis.

(Third Modification)

As shown in the lower part of FIG. 5, the X-ray imaging apparatus 1 sets the line-of-sight direction G1 corresponding to the direction orthogonal to the detection surface of the FPD 24a in the XYZ coordinate system, that is, the positive direction of the W-axis. However, it is not limited to this case. The condition setting function 315 may set the line-of-sight direction in addition to the viewpoint. In that case, the pseudo data generating function 316 generates pseudo image data by projecting the volume data along the set line-of-sight direction.

For example, the condition setting function 315 of the X-ray imaging apparatus 1 may detect a curve L such as a boundary line of the 7th to 8th thoracic spine using the volume data region N, set the line-of-sight direction along the curve L, and set the viewpoint based on the line-of-sight direction. Since the method for detecting the curve L is the same as the method described in the first modification, the description thereof will be omitted.

FIG. 10 shows a curve L such as a boundary line of the 7th to 8th thoracic spine set in the volume data region N. The line-of-sight direction G4 is set in the direction along the curve L so as to simulate X-ray-irradiation along the boundaries of the 7th to 8th thoracic spine. The condition setting function 315 calculates the distance acquired by subtracting the set distance from the second SID converted into the UVW coordinate system, and sets a position separated from the curve L (end point Q, end point R, or the midpoint between the end point Q and the end point R) in the volume data region N by a calculated distance as the viewpoint F4. However, it is not limited to this case. The condition setting function 315 may regard the set distance as "0". In that case, a position separated from the projection plane P by a distance corresponding to the second SID converted into the UVW coordinate system is set as the viewpoint F4. Here, the line-of-sight direction G4 follows a straight line connecting the end point Q and the end point R of the curve L in the volume data region N. The line-of-sight direction G4 has an angle from the direction corresponding to the direction orthogonal to the detection surface of the FPD 24a in the XYZ coordinate system, that is, the positive direction of the W-axis.

According to the third modification of the medical image processing apparatus 12 such as a console, pseudo image data is generated when X-rays are incident along a curve L such as the boundary line of the 7th to 8th thoracic spine. As a result, it is possible to provide the operator with pseudo image data useful for diagnosis.

(Fourth Modification)

As shown in the lower part of FIG. 5, the X-ray imaging apparatus 1 sets the line-of-sight direction G1 corresponding to the direction orthogonal to the detection surface of the FPD 24a in the XYZ coordinate system, that is, the positive direction of the W-axis. However, it is not limited to this case. The condition setting function 315 may set the line-of-sight direction in addition to the viewpoint. In that case, the pseudo data generating function 316 generates pseudo image data by projecting the volume data along the set line-of-sight direction.

For example, the condition setting function 315 of the X-ray imaging apparatus 1 sets the line-of-sight direction corresponding to the pseudo image data having the highest contrast. In that case, the condition setting function 315 projects the volume data along a plurality of line-of-sight directions, so the pseudo data generating function 316 generates pseudo image data candidates. Then, the pseudo data generating function 316 extracts the candidate of the pseudo image data having the highest contrast from the multiple pseudo image data candidates as the pseudo image data.

According to the fourth modification of the medical image processing apparatus 12 such as a console, it is possible to provide the operator with pseudo image data having excellent contrast and useful for diagnosis.

(Fifth Modification)

The method that, based on the volume data, the condition setting function 315 and the pseudo data generating function 316 set one viewpoint and one line-of-sight direction for one region of interest and generate one pseudo image data has been described. However, it is not limited to this case. For example, the condition setting function 315 may set viewpoints using the second SID converted into the UVW coordinate system, and set directions corresponding to the directions orthogonal to the detection surfaces of the FPD 24a. In that case, the pseudo data generating function 316 generates multiple pseudo image data in the V-axis direction by projecting the volume data from the set viewpoints along the set directions. The pseudo data generating function 316 may also generate long image data by connecting the multiple pseudo image data.

Further, for example, the condition setting function 315 may set viewpoints by using the second SID converted into the UVW coordinate system, and set directions orthogonal to the regions of interest J (shown in FIGS. 8 and 9) included in the volume data, respectively. In that case, the pseudo data generating function 316 generates multiple pseudo image data in the V-axis direction by projecting the volume data from the set viewpoints along the set directions. The pseudo data generating function 316 may also generate long image data by connecting multiple pseudo image data.

(Sixth Modification)

The configuration example in which tomosynthesis imaging is performed has been described with reference to FIG. 2. However, the configuration for performing tomosynthesis imaging is not limited to the configuration in which the fixed FPD 24a is irradiated with X-rays from the X-ray tube 23a that is linearly slid in the Y-axis direction. For example, the X-ray tube 23a that is linearly slid in the Y-axis direction may irradiate the FPD 24a that is linearly slid in the Y-axis direction with X-rays.

As shown in FIG. 11, when the X-ray tube 23a is linearly slid in the positive direction of the Y-axis, the FPD 24a is slid linearly in the negative direction of the Y-axis to perform tomosynthesis imaging. Further, the X-ray tube 23a is not limited to the case where the X-ray tube 23a is linearly slid in the Y-axis direction. Tomosynthesis imaging may be performed by moving in an arc centered on the midpoint between the focal point of the X-ray tube 23a and the center of the FPD 24a. Further, the X-ray tube 23a and the FPD 24a may be held by an arm (not shown) that can rotate and move in an arc about the midpoint between the focal point of the X-ray tube 23a and the center of the FPD 24a. In that case, tomosynthesis imaging is performed by rotating the arm that is moved in an arc.

Second Embodiment

FIG. 12 shows the medical image processing apparatus 80 according to the second embodiment. The medical image processing apparatus 80 is a workstation, an image reading terminal, or the like, and is connected to the X-ray imaging apparatus 1 or the medical image managing apparatus (e.g., image server) 70 via a network so as to be capable of intercommunication. The medical image processing apparatus 80 may be an offline device or may have the function of the medical image managing apparatus 70.

The medical image processing apparatus 80 includes processing circuitry 81, a memory 82, an input interface 84, a display 85, and a network interface 86. The processing circuitry 81, the memory 82, the input interface 84, the display 85, and the network interface 86 are equivalent to the processing circuitry 31, the memory 32, the input interface 34, the display 35, and the network interface 36 shown in FIG. 1, respectively. The description will be omitted assuming that they have the same configuration.

The processing circuitry 81 reads and executes a computer program stored in the memory 82 or directly embedded in the processing circuitry 81, thereby realizing a volume acquiring function 814, a condition setting function 815, and a pseudo data generating function 816. Hereinafter, the case where the functions 814 to 816 function as software will be described as an example, but all or a part of the functions 814 to 816 may be realized by a circuit such as an ASIC. Further, the functions 814 to 816 may be separated and performed by multiple devices in the medical image system.

The memory 82 stores volume data generated by the volume generating function 313 (shown in FIG. 3) and acquired from the X-ray imaging apparatus 1 or the medical image managing apparatus 70 via the network interface 86. Alternatively, the memory 82 stores the volume data generated by the volume generating function 313 (shown in FIG. 3) and acquired from the X-ray imaging apparatus 1 or the medical image managing apparatus 70 via the portable storage medium.

The volume acquiring function 814 has a function of acquiring volume data from the memory 82. The volume acquiring function 814 has the same function as the volume acquiring function 314 shown in FIG. 3. The volume acquiring function 814 is an example of a volume acquiring unit.

The condition setting function 815 has a function equivalent to the condition setting function 315 shown in FIG. 3. The condition setting function 815 is an example of a condition setting unit.

The pseudo data generating function 816 has a function equivalent to the pseudo data generating function 316 shown in FIG. 3. The pseudo data generating function 816 is an example of a pseudo data generating unit.

Since an operation of the medical image processing apparatus 80 is the same as the operation of steps ST5 to ST8 of the medical image processing apparatus 12 shown in FIG. 7, the description thereof will be omitted.

By using the medical image processing apparatus 80, which is a workstation, connected to the X-ray imaging apparatus 1 or the medical image managing apparatus 70 via a network, or using the offline medical image processing apparatus 80, pseudo image data corresponding to the second SID larger than the first SID can be generated based on the image data acquired by the first SID. As a result, the medical image processing apparatus 80 makes it possible to provide the operator with pseudo image data useful for diagnosis in consideration of the incident position and the incident angle on the examination target M.

According to at least one embodiment described above, it is possible to provide X-ray image data useful for diagnosis.

While certain embodiments have been described, these embodiments have been presented by way of example only, and are not intended to limit the scope of the inventions. Indeed, the novel methods and systems described herein may be embodied in a variety of other forms; furthermore, various omissions, substitutions, changes, and combinations of embodiments in the form of the methods and systems described herein may be made without departing from the spirit of the inventions. The accompanying claims and their equivalents are intended to cover such forms or modifications as would fall within the scope and spirit of the inventions.

What is claimed is:

1. An medical image processing apparatus comprising:
processing circuitry configured to
acquire volume data generated based on tomosynthesis imaging of a subject,
set a virtual focal point at a position different from a focal position in the tomosynthesis imaging, and
generate a pseudo projection image based on the virtual focal point and the volume data.

2. The medical image processing apparatus according to claim 1, wherein
the processing circuitry is configured to set a region of interest in the pseudo projection image, and modify the virtual focal point to a position where contrast of the region of interest meets a predetermined reference.

3. The medical image processing apparatus according to claim 1, wherein
the processing circuitry is configured to set the virtual focal point projected in a predetermined direction with respect to a region of interest included in the volume data.

4. The medical image processing apparatus according to claim 1, wherein
the processing circuitry is configured to
set virtual focal points to be projected in directions orthogonal to regions of interest included in the volume data, respectively,
generate pseudo projection images based on the virtual focal points and the regions of interest, and
synthesize the pseudo projection images.

5. The medical image processing apparatus according to claim 1, wherein
the processing circuitry is configured to
acquire the volume data as volume data generated based on X-ray imaging by a first SID (Source Image Distance),
set a viewpoint corresponding to the virtual focal point based on a second SID that is larger than the first SID, and
generate projection data acquired by projecting the volume data from the viewpoint along a line-of-sight direction as the pseudo projection image.

6. The medical image processing apparatus according to claim 5, wherein
the processing circuitry is configured to set a position separated from a position of a projection plane by a distance corresponding to the second SID as the viewpoint.

7. The medical image processing apparatus according to claim 5, wherein
the processing circuitry is configured to
calculate a distance acquired by subtracting a set distance from the second SID, and
set a position separated from the volume data by the calculated distance as the viewpoint.

8. The medical image processing apparatus according to claim 5, wherein
the processing circuitry is configured to set a position separated from a position of a projection plane by a distance corresponding to the second SID as the viewpoint.

9. The medical image processing apparatus according to claim 5, wherein
the processing circuitry is configured to
calculate a distance acquired by subtracting a set distance from the second SID, and
set a position separated from a position of a region of interest set in the volume data by the calculated distance as the viewpoint.

10. The medical image processing apparatus according to claim 5, wherein
the processing circuitry is configured to
set the line-of-sight direction in addition to the viewpoint, and
generate the pseudo projection image by projecting the volume data from the viewpoint along the line-of-sight direction.

11. The medical image processing apparatus according to claim 10, wherein
the processing circuitry is configured to set a direction corresponding to a direction orthogonal to a detection surface of an X-ray detector as the line-of-sight direction.

12. The medical image processing apparatus according to claim 10, wherein
the processing circuitry is configured to set, as the line-of-sight direction, a direction orthogonal to a region of interest included in the volume data.

13. The medical image processing apparatus according to claim 10, wherein
the processing circuitry is configured to set, as the line-of-sight direction, a line-of-sight direction corresponding to the pseudo projection image having the highest contrast.

14. The medical image processing apparatus according to claim 10, wherein
the processing circuitry is configured to
set viewpoint elements as the viewpoint, set line-of-sight direction elements corresponding to directions orthogonal to detection surfaces of an X-ray detector as the line-of-sight direction, and generate pseudo projection images as the pseudo projection image by projecting the volume data from the viewpoint along the line-of-sight direction, respectively.

15. The medical image processing apparatus according to claim 10, wherein the processing circuitry is configured to set multiple viewpoints as the viewpoint, set, as the line-of-sight direction, multiple line-of-sight directions orthogonal to regions of interest included in the volume data, and generate, as the pseudo projection image, multiple pseudo projection images by projecting the volume data from the viewpoints along the line-of-sight directions, respectively.

16. An X-ray imaging apparatus comprising:

an X-ray irradiator configured to irradiate X-rays;

an X-ray detector configured to detect the X-rays; and processing circuitry configured to acquire volume data generated based on tomosynthesis imaging of a subject, set a virtual focal point at a position different from a focal position in the tomosynthesis imaging, and generate a pseudo projection image based on the virtual focal point and the volume data.

17. The X-ray imaging apparatus according to claim 16, wherein the processing circuitry is configured to generate projection images corresponding to irradiation directions based on an X-ray imaging of a first SID, generate volume data from the projection images and stores them in a memory;

acquire the volume data from the memory, set a viewpoint corresponding to the virtual focus based on a second SID that is larger than the first SID, and generate projection data acquired by projecting the volume data from the viewpoint along a line-of-sight direction as the pseudo projection image.

* * * * *